(12) United States Patent
Takemoto et al.

(10) Patent No.: US 10,487,183 B2
(45) Date of Patent: Nov. 26, 2019

(54) METHOD OF BONDING SUBSTRATES AND METHOD OF PRODUCING MICROCHIP

(71) Applicant: Ushio Denki Kabushiki Kaisha, Tokyo (JP)

(72) Inventors: Fumitoshi Takemoto, Tokyo (JP); Shinji Suzuki, Tokyo (JP); Motohiro Sakai, Tokyo (JP); Kenichi Hirose, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/317,469

(22) PCT Filed: Jun. 27, 2017

(86) PCT No.: PCT/JP2017/023519
§ 371 (c)(1),
(2) Date: Jan. 11, 2019

(87) PCT Pub. No.: WO2018/012276
PCT Pub. Date: Jan. 18, 2018

(65) Prior Publication Data
US 2019/0300662 A1    Oct. 3, 2019

(30) Foreign Application Priority Data

Jul. 15, 2016  (JP) .................. 2016-140138

(51) Int. Cl.
*C08J 5/12* (2006.01)
*C08J 7/12* (2006.01)
(Continued)

(52) U.S. Cl.
CPC .............. *C08J 5/121* (2013.01); *B29C 65/02* (2013.01); *B29C 66/028* (2013.01);
(Continued)

(58) Field of Classification Search
CPC ...... C08J 5/121; B29C 65/02; B29C 66/7465; B32B 17/064
See application file for complete search history.

(56) References Cited

U.S. PATENT DOCUMENTS

2004/0211511 A1   10/2004  Suzuki
2009/0214856 A1    8/2009  Gomi
2014/0027054 A1*   1/2014  Yoshihara ........... B29C 65/1432
                                                 156/273.3

FOREIGN PATENT DOCUMENTS

JP        3714338 B2    11/2005
JP     2006-187730 A     7/2006
(Continued)

OTHER PUBLICATIONS

International Search Report issued in PCT/JP2017/023519; dated Aug. 1, 2017.
Written Opinion issued in PCT/JP2017/023519; dated Aug. 1, 2017.

*Primary Examiner* — Carson Gross
(74) *Attorney, Agent, or Firm* — Studebaker & Brackett PC

(57) ABSTRACT

The present invention has as its object the provision of a method of bonding substrates, which can bond two substrates, at least one of which has warpage and undulation of a bonding surface, in a high adhesion state and a method of producing a microchip.
In the method of bonding substrates according to the present invention, the first substrate is formed of a material having a deformable temperature at which the substrate deforms and which is higher than a deformable temperature of the second substrate, the method includes: a surface activation step of activating each of bonding surfaces of the first substrate and the second substrate; a stacking step of stacking the first substrate and the second substrate so that the respective bonding surfaces thereof are in contact with each
(Continued)

other; and a deforming step of deforming the bonding surface of the second substrate to conform to a shape of the bonding surface of the first substrate, and the deforming step is performed by heating the stacked body of the first substrate and the second substrate obtained in the stacking step at a temperature not lower than the deformable temperature of the second substrate and lower than the deformable temperature of the first substrate.

6 Claims, 3 Drawing Sheets

(51) Int. Cl.
*H05K 3/30* (2006.01)
*B29C 65/02* (2006.01)
*B29C 65/00* (2006.01)
*B32B 37/06* (2006.01)
*B32B 17/06* (2006.01)
*B32B 38/00* (2006.01)
*B29L 31/34* (2006.01)

(52) U.S. Cl.
CPC ........ *B29C 66/7465* (2013.01); *B32B 17/064* (2013.01); *B32B 37/06* (2013.01); *B32B 38/0008* (2013.01); *C08J 7/123* (2013.01); *H05K 3/305* (2013.01); *B29L 2031/34* (2013.01); *B32B 2457/00* (2013.01); *C08J 2333/00* (2013.01); *C08J 2345/00* (2013.01); *H05K 2203/095* (2013.01)

(56) References Cited

FOREIGN PATENT DOCUMENTS

| | | | |
|---|---|---|---|
| JP | 2006187730 A | * | 7/2006 |
| JP | 2008-019348 A | | 1/2008 |
| JP | 2008019348 A | * | 1/2008 |
| JP | 2008-290027 A | | 12/2008 |
| JP | 2009-197169 | | 9/2009 |
| JP | 5152361 B2 | | 2/2013 |
| WO | 2008/087800 A1 | | 7/2008 |
| WO | 2016/060080 A1 | | 4/2016 |

* cited by examiner

Fig. 2
(a-1) 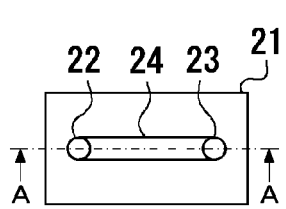
(a-2) 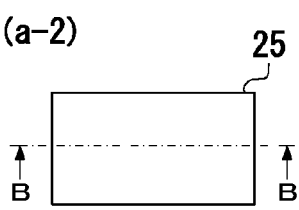
(b-1) 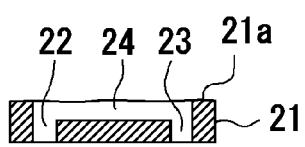
(b-2) 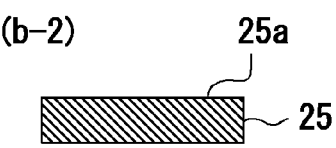
(c) 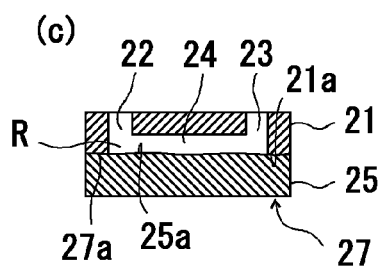

METHOD OF BONDING SUBSTRATES AND METHOD OF PRODUCING MICROCHIP

TECHNICAL FIELD

The present invention relates to a method of bonding two substrates and a method of producing a microchip.

BACKGROUND ART

In the field of biochemistry, attention has been paid to techniques for separating, synthesizing, extracting or analyzing trace amounts of reagents using microreactors. The microreactor is composed of a microchip in which channels for microscale analysis and the like are formed on a small substrate formed of, for example, silicon, a silicone resin or glass by a semiconductor microfabrication technique.

A reaction analysis system using such a microreactor is called a micro total analysis system (hereinafter referred to as "µTAS"). According to the µTAS, since the ratio of the surface area to the volume of the reagent becomes large, a high-speed and high-precision reaction analysis can be performed and a compact automated system can also be realized.

In the microchip, a microchip suitable for various applications can be formed by providing a functional region having various functions such as a reaction region in which a reagent is disposed in a flow path called a microchannel. As applications of the microchip, may be mentioned analysis in the fields of chemistry, biochemistry, pharmacology, medicine, and veterinary medicine, such as gene analysis, clinical diagnosis, drug screening, and the like, and synthesis of compounds, environmental measurement, and the like.

In such a microchip, a pair of microchip substrates are typically bonded to each other so as to face each other, and a minute flow path having a width of, for example, 10 to several hundred µm and a depth of, for example, 10 to several hundred µm is formed in a surface of at least one of the microchip substrates. As the microchip substrate, a glass substrate is mainly adopted because it is easy to produce and optical detection is possible. Recently, development of a microchip using an inexpensive synthetic resin substrate, which is lighter in weight but harder to break than a glass substrate, has been promoted.

In the production of the microchip, as a method of bonding two microchip substrates to each other, a method of bonding with an adhesive, a method of thermal fusion bonding, or the like is conceivable.

However, these methods have the following problems. That is, in the method of bonding with an adhesive, there may be possible problems that the adhesive seeps into the minute flow path and so the flow path may be clogged, that part of the minute flow path may be narrowed and the diameter of the flow path may become uneven, and that disturbance may occur in the uniform characteristic on the wall surface of the flow path. In addition, in the method of bonding by thermal fusion, there may be problems that, if fusion bolding is performed at a temperature not lower than the heat melting temperature, the flow path may be crushed at the heating step, and that the flow path may not be maintained in a predetermined cross-sectional shape, and so it is difficult to sophisticate the functions of the microchip.

Therefore, there has been proposed a method of irradiating vacuum ultraviolet rays to each of the bonding surfaces of two substrates, or converting a process gas into plasma under atmospheric pressure or in the vicinity thereof and bringing the plasma-converted process gas into contact with the surface of the substrate, thereby activating the bonding surface of each substrate, and then stacking and bonding the two substrates so that the bonding surfaces are brought into contact with each other (see, for example, Patent Literature 1 to Patent Literature 5).

In addition, there has also been proposed a method of allowing a bonding film to be interposed between two substrates, and irradiating the bonding film with ultraviolet rays to develop adhesiveness of the bonding film, thereby bonding the two substrates by the adhesiveness (see, for example, Patent Literature 6).

CITATION LIST

Patent Literature

Patent Literature 1: Japanese Patent No. 3714338
Patent Literature 2: Japanese Patent Application Laid-Open No. 2006-187730
Patent Literature 3: Japanese Patent Application Laid-Open No. 2008-19348
Patent Literature 4: International Publication No. 2008/087800A1
Patent Literature 5: Japanese Patent No. 5152361
Patent Literature 6: Japanese Patent Application Laid-Open No. 2009-197169

SUMMARY OF INVENTION

Technical Problem

In recent years, microchips capable of coping with various measurements such as simultaneous measurement of a plurality of specimens and multiple measurements with different measurement methods, have been investigated.

In order to realize such a microchip, it is necessary to incorporate a plurality of measurement detection units in one microchip, to construct various measurement structures corresponding to a plurality of measurement methods in the measurement detection unit, and the like. Therefore, such one microchip inevitably becomes large in size.

A large-sized microchip has, for example, a size of about 85 mm×128 mm in length and width, and the thickness of each of the two microchip substrates constituting the microchip is, for example, several mm or more.

However, in such a large-sized microchip, the following problems may arise.

As described above, a typical microchip has a structure in which a pair (two) of microchip substrates are bonded to each other in an opposed manner. In a large-sized microchip, the pair of microchip substrates themselves naturally become large. As a result, undulation of the bonding surface of each microchip substrate, warpage of the microchip substrate itself and the like, which are inevitably possessed by each of the microchip substrates, have a large influence on the bonded state of the pair of microchip substrates.

That is, when the pair of microchip substrates are stacked on each other, the entire bonding surfaces may not be in close contact with each other due to the undulation of the bonding surface of the microchip substrate or the warpage of the microchip substrate itself.

FIG. 3 includes explanatory diagrams schematically illustrating an example of a method of producing a conventional microchip.

A method of producing a microchip will be specifically described. First, each of a bonding surface 51a of a first microchip substrate 51 and a bonding surface 55a of a second microchip substrate 55 is irradiated with vacuum ultraviolet rays L emitted from an ultraviolet light source 59 ((a-1) and (a-2) of FIG. 3). Here, it is assumed that undulation (portions surrounded by dotted lines in FIG. 3) has occurred on the bonding surface 51a of the first microchip substrate 51.

Next, the first microchip substrate 51 and the second microchip substrate 55 are stacked so that the bonding surface 51a of the first microchip substrate 51 and the bonding surface 55a of the second microchip substrate 55 are in contact with each other. In the obtained stacked body 50, slight spaces S are formed in the portions having the undulation due to the bonding surface 51a of the first microchip substrate 51 ((b) of FIG. 3).

Further, the stacked body 50 is pressurized and heated ((c) of FIG. 3). By the application of pressure and heat in this manner, the bonded body 57 is obtained. In the bonded body 57, in some cases, the spaces S may disappear and so the entire bonding surfaces 51a and 55a of the first microchip substrate 51 and the second microchip substrate 55 may be in close contact with each other to be satisfactorily bonded; however, as shown in (d) of FIG. 3, the spaces S are not disappeared and often remain as a bonding defective portion in many cases.

As described above, when not only the microchip substrates, but also the larger substrates to be bonded are adopted, problems are likely to occur in which a defective portion of the bonding between the substrates occurs due to the undulation of the bonding surfaces of the substrates or the warpage of the substrate itself, or air bubbles or the like are caught between the bonded surfaces of the two substrates.

In addition, when two substrates are bonded in a state in which there is undulation of the bonding surfaces of the substrates or warpage of the substrates themselves, stress concentration occurs in part of the bonded body due to the aforementioned undulation or warpage. In some cases, there may be a problem that at least a partial region of the substrate that has originally been bonded may peel off due to the stress concentration.

In addition, when air bubbles are present in between the bonded surfaces of the bonded body, this may cause noise in performing optical measurement.

Due to the above-mentioned problems, it is difficult to produce a microchip with a relatively large size, and for example, it is only possible to produce a microchip with a size as small as a slide glass. For this reason, it has been difficult to incorporate a plurality of measurement detection units in one microchip or to construct various measurement structures corresponding to a plurality of measurement methods in the measurement detection unit.

When the thickness of the microchip substrate is as thin as, for example, about 10 μm, it is possible to improve the adhesiveness of the bonded surfaces of the two microchip substrates because the flexibility of the microchip substrate becomes high. In contrast, when a large-sized microchip is to be produced, the thickness of each microchip substrate needs to be several mm or more, and therefore it is difficult to select such a technique.

The present invention has been made in view of the foregoing circumstances and has as its object the provision of a method of bonding substrates, which can bond two substrates, at least one of which has warpage and undulation of a bonding surface, in a high adhesion state and a method of producing a microchip.

Solution to Problem

A method of bonding substrates according to the present invention is a method of bonding a first substrate and a second substrate, each formed of glass or a resin, to each other, wherein the first substrate is formed of a material having a deformable temperature at which the substrate deforms and which is higher than a deformable temperature of the second substrate, the method comprises:
  a surface activation step of activating each of a bonding surface of the first substrate and a bonding surface of the second substrate;
  a stacking step of stacking the first substrate and the second substrate so that the respective bonding surfaces thereof are in contact with each other; and
  a deforming step of deforming the bonding surface of the second substrate to conform to a shape of the bonding surface of the first substrate, and the deforming step is performed by heating a stacked body of the first substrate and the second substrate obtained in the stacking step at a temperature not lower than the deformable temperature of the second substrate and lower than the deformable temperature of the first substrate.

In the method of bonding substrates according to the present invention, it is preferable that the two stacked substrates are pressurized in a direction in which they approach each other in the deforming step.

In the method of bonding substrates according to the present invention, the surface activation step may be an ultraviolet irradiation treatment step of irradiating each of the bonding surface of the first substrate and the bonding surface of the second substrate with vacuum ultraviolet rays.

In the method of bonding substrates according to the present invention, the surface activation step may be a plasma gas treatment step of bringing a process gas which has been converted into plasma by atmospheric pressure plasma into contact with each of the bonding surface of the first substrate and the bonding surface of the second substrate.

In a method of producing a microchip according to the present invention, a flow path forming portion is provided in at least one bonding surface of a first substrate and a second substrate in the first substrate and the second substrate, each formed of glass or a resin, the method comprising bonding the first substrate and the second substrate to each other by the method of bonding substrates described above to obtain a microchip having a flow path through which a medium flows.

In the method of producing a microchip according to the present invention, it is preferable that the flow path forming portion is provided only in the bonding surface of the first substrate.

Advantageous Effects of Invention

According to the method of bonding substrates of the present invention, only the second substrate is softened by heating at a temperature not lower than the deformable temperature of the second substrate and lower than the deformable temperature of the first substrate in the deforming step, and so the bonding surface of the second substrate can be deformed to conform to the shape of the bonding surface of the first substrate, whereby the entire bonded surfaces of the bonded body can be reliably made in close contact with each other. Accordingly, the first substrate and the second substrate, at least one of which has warpage or undulation of the bonding surface, can be bonded to each other in a high adhesion state.

According to the method of producing a microchip of the present invention, since the bonding surface of the second substrate is deformed to conform to the shape of the bonding surface of the first substrate by performing the deforming step, the entire bonded surfaces of the obtained microchip can be reliably made in close contact with each other. Therefore, the first substrate and the second substrate, for example, large-area microchip substrates, at least one of which has warpage or undulation of the bonding surface, can be bonded to each other in a high adhesion state. As a result, even in a large-sized microchip, intended flow paths can be formed with high reliability.

BRIEF DESCRIPTION OF DRAWINGS

FIG. 2 includes explanatory diagrams schematically illustrating an example of a method of producing a microchip according to the present invention.

DESCRIPTION OF EMBODIMENTS

Hereinbelow, a description will be given of embodiments of the present invention.

Figure 1:
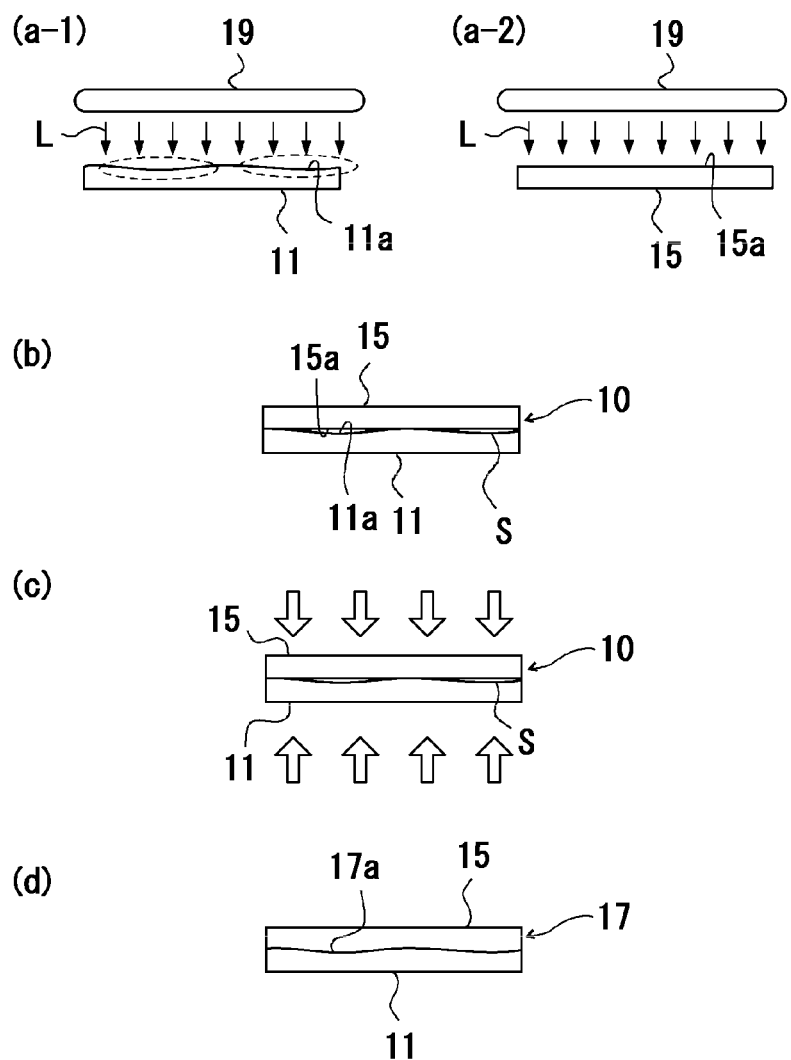
FIG. 1 includes explanatory diagrams schematically illustrating an example of a method of bonding substrates according to the present invention.
Figure 3:
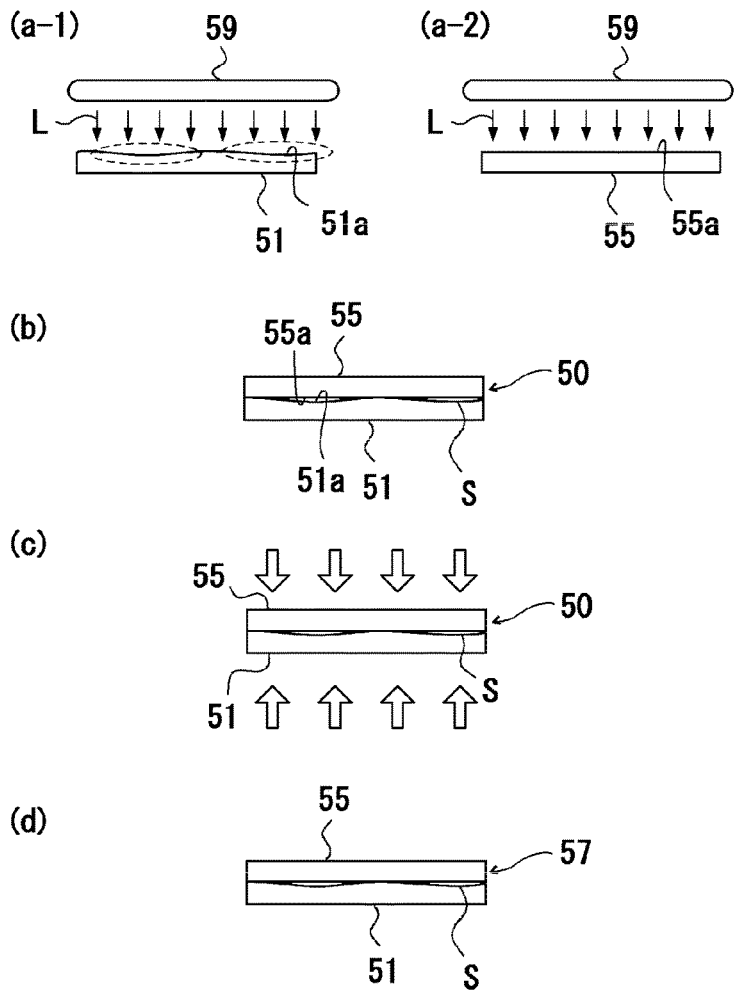
FIG. 3 includes explanatory diagrams schematically illustrating an example of a method of producing a conventional microchip.

Method of Bonding Substrates:

FIG. 1 includes explanatory diagrams schematically illustrating an example of a method of bonding substrates according to the present invention.

The method of bonding substrates of the present invention includes: a surface activation step ((a-1) and (a-2) of FIG. 1) of activating each of a bonding surface 11a of a first substrate 11 and a bonding surface 15a of a second substrate 15; a stacking step ((b) of FIG. 1) of stacking the first substrate 11 and the second substrate 15 so that the respective bonding surfaces 11a and 15a are in contact with each other; and a deforming step ((c) of FIG. 1) of deforming the bonding surface 15a of the second substrate 15 to conform to the shape of the bonding surface 11a of the first substrate 11.

Substrate:

Each of the first substrate 11 and the second substrate 15 adopted by the present invention is formed of a material selected from the group consisting of glass and a synthetic resin.

As the synthetic resin constituting the substrates 11 and 15, may be used a silicone resin, a cycloolefin resin (cycloolefin polymer (COP), cycloolefin copolymer (COC) or the like), and an acrylic resin. For example, when the substrates 11 and 15 are each a microchip substrate, it is preferable to use a material having excellent light transmittance, and as a resin having excellent light transmittance, for example, an acrylic resin or a cycloolefin resin may be used.

As the glass constituting the substrates 11 and 15, may be used quartz glass, alkali glass, borosilicate glass or the like.

In the present invention, the deformable temperature of a substrate is a temperature at which the substrate is deformed, and specifically, refers to a temperature of $(Tg-10)°$ C. which is slightly lower than the glass transition temperature (Tg) of the material constituting the substrate. The deformable temperature of the substrate may vary slightly depending on the amount of resin input, the holding pressure, and the rate of temperature drop during injection molding.

The first substrate 11 and the second substrate 15 are formed of respective materials configured such that the deformable temperature of the first substrate 11 is higher than the deformable temperature of the second substrate 15.

That is, suppose that the glass transition temperature of the first substrate 11 is Tg1 and the glass transition temperature of the second substrate 15 is Tg2. In this case, the deformable temperatures of the first substrate 11 and the second substrate 15 satisfy the relationship: $(Tg1-10) > (Tg2-10)$.

The sizes of the first substrate 11 and the second substrate 15 are, for example, 85 mm×128 mm in length and width, and each 1 to 3 mm in thickness.

According to the method of bonding substrates of the present invention, even in the case of a thick substrate having a thickness of, for example, 1 to 3 mm as described in detail below, the bonding surface 15a of the second substrate 15 can be deformed to conform to the shape of the bonding surface 11a of the first substrate 11, and the entire bonded surfaces 17a of the bonded body 17 obtained can be effectively made in close contact with each other.

Surface Activation Step:

Preferably, the surface activation step is an ultraviolet irradiation treatment step of irradiating vacuum ultraviolet rays L to each of the bonding surface 11a of the first substrate 11 and the bonding surface 15a of the second substrate 15, or a plasma gas treatment step of bringing the process gas, which has been converted into plasma by atmospheric pressure plasma, into contact with each of the bonding surface of the first substrate and the bonding surface of the second substrate. FIG. 1 illustrates the ultraviolet irradiation treatment step performed.

(1) Ultraviolet Irradiation Treatment Step

When the ultraviolet irradiation treatment step is selected as the surface activation step, vacuum ultraviolet rays L having a wavelength of not more than 200 nm are irradiated from an ultraviolet light source 19 onto the bonding surfaces 11a and 15a of the substrates 11 and 15.

As the ultraviolet light source 19, for example, may be suitably used an excimer lamp such as a xenon excimer lamp having an emission line at a wavelength of 172 nm, a low-pressure mercury lamp having an emission line at a wavelength of 185 nm, or a deuterium lamp having an emission line in a wavelength range of 120 to 200 nm.

The irradiance of the vacuum ultraviolet rays L irradiated to the bonding surfaces 11a and 15a of the substrates 11 and 15 is, for example, 10 to 100 $mW/cm^2$.

The irradiation time of the vacuum ultraviolet rays L to the bonding surfaces 11a and 15a of the substrates 11 and 15 is appropriately set depending on the materials constituting the substrates 11 and 15, and is preferably, for example, not less than 5 seconds, and more preferably 10 to 60 seconds.

(2) Plasma Gas Treatment Step

When a plasma gas treatment step is selected as the surface activation step, a process gas that has been converted into plasma by atmospheric pressure plasma is brought into contact with the bonding surface of the substrate.

As the process gas, it is preferable to use a gas containing nitrogen gas, argon gas or the like as a main component and oxygen gas in an amount of 0.01 to 5% by volume. Alternatively, a mixed gas of nitrogen gas and clean dry air (CDA) may be used.

The treatment time by the plasma gas treatment is, for example, 5 to 100 seconds.

By performing the surface activation treatment on the substrates in this manner, the bonding surfaces 11a and 15a of the substrates 11 and 15 are in a state suitable for bonding, that is, a state in which terminals are substituted with a hydroxy group (OH group) or a carboxyl group (COOH group).

Stacking Step:

In the stacking step, as shown in (b) of FIG. 1, the first substrate 11 and the second substrate 15 are stacked in a state in which the bonding surface 11a of the first substrate 11 and the bonding surface 15a of the second substrate 15 are in contact with each other in a room temperature environment.

Through this stacking step, a stacked body 10 in which the first substrate 11 and the second substrate 15 are stacked is obtained.

Here, it is assumed that undulation (portions surrounded by dotted lines in FIG. 1) occurs on the bonding surface 11a of the first substrate 11. Therefore, in the obtained stacked body 10, spaces S are formed in the portions having the undulation due to the bonding surface 11a of the first substrate 11.

In the example of FIG. 1, it is assumed that the second substrate 15 does not undulate. However, even if the second substrate 15 is undulated or warped, the effect of the present invention can be obtained.

Deforming Step:

In the deforming step, the stacked body 10 obtained in the stacking step can be heated to thereby deform the bonding surface 15a of the second substrate 15 to conform to the shape of the bonding surface 11a of the first substrate 11.

<Heating Condition>

The heating temperature is a temperature not lower than the deformable temperature of the second substrate 15 and lower than the deformable temperature of the first substrate 11, and the heating time is, for example, 60 to 300 seconds.

In this deforming step, it is preferable to pressurize the two substrates 11 and 15 of the stacked body 10 in a direction in which they approach each other simultaneously with the heating and/or before and after the heating. In (c) of FIG. 1, the pressurizing force on the stacked body 10 is indicated by a white arrow for the sake of convenience.

For example, the pressurization to the stacked body 10 may be performed under a predetermined pressurization condition, or may be performed in a plurality of stages, for example, in two stages, by appropriately adjusting the processing conditions.

The pressurization condition may be appropriately set depending on a material constituting the substrate and the heating temperature.

Specific pressurization conditions may include a pressurizing force of, for example, 0.1 to 5 MPa and a pressurizing time of, for example, 60 to 300 seconds. Further, in the case where the pressurizing treatment for the substrate is performed in two stages, for example, the pressurizing force in the second pressurizing treatment may be set to be smaller than the pressurizing force in the first pressurizing treatment within the above-described numerical range. The pressurizing time in the second pressurizing treatment may be set to be longer than the pressurizing time in the first pressurizing treatment within the above-described numerical range.

In this deforming step, the second substrate 15 is deformed as follows. That is, when the stacked body 10 is heated at a temperature which is not lower than the deformable temperature of the second substrate 15 and lower than the deformable temperature of the first substrate 11, the second substrate 15 is softened. On the other hand, since the temperature of the first substrate 11 itself does not reach the glass transition temperature, the first substrate 11 does not soften and maintains the rigidity thereof. Therefore, only the second substrate 15 is softened, and so the shape of the bonding surface 15a of the second substrate 15 is deformed to conform to the shape of the undulation of the bonding surface 11a of the first substrate 11. Thus, the space S in the stacked body 10 disappears, and as shown in (d) of FIG. 1, the bonding surface 11a of the first substrate 11 and the bonding surface 15a of the second substrate 15 come into uniformly contact with each other over the entire surface. As a result, it is possible to avoid occurrence of a bonding defective portion between the substrates and air bubbles residing in between the bonded surfaces of the two substrates, thereby obtaining a good adhesion state between the first substrate 11 and the second substrate 15.

Then, the first substrate 11 and the second substrate 15 are bonded to each other through various chemical reaction processes, for example, by hydrogen bonding between an OH group at the terminal end of the bonding surface 11a of the first substrate 11 and an OH group at the terminal end of the bonding surface 15a of the second substrate 15, or by covalent bonding obtained by dehydration condensation therefrom, whereby the bonded body 17 in which the first substrate 11 and the second substrate 15 are bonded firmly to each other is obtained.

According to the method of bonding substrates as described above, since only the second substrate 15 is softened by heating at a temperature not lower than the deformable temperature of the second substrate 15 and lower than the deformable temperature of the first substrate 11 in the deforming step, the bonding surface 15a of the second substrate 15 can be deformed to conform to the shape of the bonding surface 11a of the first substrate 11, and the entire bonded surfaces 17a of the bonded body 17 can be reliably made in close contact with each other. Therefore, the first substrate 11 and the second substrate 15, at least one of which has warpage or undulation of the bonding surface, can be bonded to each other in a high adhesion state.

Method of Producing Microchip:

The method of producing a microchip according to the present invention is a method of obtaining a microchip having a flow path through which a medium flows by using the above-described method of bonding substrates.

Specifically, in the first substrate and the second substrate, each of which is formed of glass or a resin and has a different deformable temperature from each other, a flow path forming portion is provided in a bonding surface of at least one of the first substrate and the second substrate, preferably, only in a bonding surface of a substrate having a higher deformable temperature (the first substrate in the present invention), and such a substrate having a flow path forming portion is adopted as the microchip substrate.

When the flow path forming portion is provided only in the bonding surface of the substrate having the higher deformable temperature (the first substrate in the present invention), the first substrate is not softened during the deforming step, and so the flow path forming portion formed in the first substrate is not crushed or deformed. Therefore, the flow path in the obtained microchip is not crushed or deformed.

FIG. 2 includes explanatory diagrams schematically illustrating an example of a method of producing a microchip according to the present invention, wherein (a-1) is a plan view of a first substrate, (b-1) is a cross-sectional view taken along line A-A, (a-2) is a plan view of a second substrate, (b-2) is a cross-sectional view taken along line B-B, and (c) is a cross-sectional view of the resulting microchip.

Specifically, in the method of producing a microchip according to the present invention, a first microchip substrate 21 and a second microchip substrate 25 are used as microchip substrates. The first microchip substrate 21 has an injection port 22 having a through hole for injecting, for example, a reagent or the like and a discharge port 23 having a through hole for discharging the reagent or the like. The first microchip substrate 21 further has a trough-shaped flow path forming portion 24 having a rectangular cross-sectional shape that communicates with the through hole of the injection port 22 and the through hole of the discharge port 23 in the bonding surface 21a (upper surface in (a-2) of FIG. 2). The necessary structural recessed portions such as the injection port 22, the discharge port 23 and the flow path forming portion 24 can be formed by a known technique such as machining or mold transfer, for example.

Although the second microchip substrate 25 does not have a structural recessed portion formed therein, it may have a structural recessed portion corresponding to the structural recessed portion of the first microchip substrate 21 in the bonding surface 25a thereof, for example.

The first microchip substrate 21 illustrated in FIG. 2 has only one set of structural recessed portions (the injection port 22, the flow path forming portion 24 and the discharge port 23) serving as a measurement circuit portion. When one first microchip substrate in which a large number of structural recessed portions serving as a large number of measurement circuit portions are formed is used, a large-sized microchip capable of providing a large number of functions can be produced.

The size of the microchip substrates 21 and 25 is, for example, 85 mm×128 mm in length and width, and the thickness thereof is, for example, 1 to 3 mm.

As an example of the dimensions of the flow path forming portion 24 of the structural recessed portion of the first microchip substrate 21, the width thereof is 150 μm, the depth thereof is 150 μm, and the length thereof is 20 mm.

In the microchip 27, which is a bonded body in which the first microchip substrate 21 and the second microchip substrate 25 are bonded, as illustrated in (c) of FIG. 2, the flow path forming portion 24 formed in the first microchip substrate 21 is hermetically sealed by the second microchip substrate 25 serving as a lid, and so the flow path R through which the medium flows is partitioned.

According to the method of producing a microchip as described above, since the bonding surface 25a of the second microchip substrate 25 is deformed to conform to the shape of the bonding surface 21a of the first microchip substrate 21 by performing the deforming step, the entire bonded surfaces 27a of the microchip 27 thus obtained can be reliably made in close contact with each other. Therefore, the first microchip substrate 21 and the second microchip substrate 25, for example, large-area microchip substrates, at least one of which has warpage or undulation of the bonding surface, can be bonded to each other in a high adhesion state. As a result, even in a large-sized microchip, intended flow paths can be formed with high reliability.

Although the embodiments of the present invention have been described above, the present invention is not limited to the above-described embodiments, and various modifications can be made thereto.

EXAMPLE

A description will next be given of specific examples of the method of boding substrates; however, the present invention is not limited to the following examples.

The following substrates A and B were prepared.

The substrate A is formed of a cycloolefin resin ("Zeonex 460R" manufactured by Zeon Corporation, deformable temperature: 120° C.).

The substrate B is formed of an acrylic resin ("Sumipex" manufactured by Sumitomo Chemical Co., Ltd., deformable temperature: 100° C.)

Each substrate is in the form of a short plate having dimensions of 100 mm×150 mm×2 mm.

The deformable temperature of each substrate corresponds to a temperature of (glass transition temperature of each substrate−10° C.)

Reference Examples 1 to 7

Two substrates B were adopted as the first substrate and the second substrate, and these substrates were bonded to each other by performing an ultraviolet irradiation treatment step and a bonding step described below. In the substrate B adopted as the first substrate, a plurality of minute flow path forming portions were provided in advance. The flow path forming portion has a width of 150 μm, a depth of 150 μm, and a length of 20 mm.

Ultraviolet Irradiation Treatment Step:

Using a xenon excimer lamp, the bonding surface of each of the two substrates was irradiated with vacuum ultraviolet rays under the conditions that the irradiance was 40 mW/cm$^2$ and the irradiation time was 20 seconds.

Bonding Step:

Two substrates B, B were stacked so that their respective bonding surfaces were in contact with each other to obtain a stacked body (Stacking Step). Next, the two substrates B, B were bonded by pressurizing the stacked body under the conditions that the pressurizing force was 0.2 MPa, the pressurizing time was 300 seconds, and the heating temperature was set as described in Table 1.

The bonded body thus obtained was visually evaluated for bonded state. Further, the fractured cross section thereof was observed to confirm the presence or absence of the deformation of the flow path. The results are shown in Table 1.

In Reference Examples 1 to 3, it was confirmed that although the two substrates B, B could be bonded to each other, the undulation of the bonding surfaces and warpage of the respective substrates could not be absorbed, and a gap was formed in a part of the bonded surfaces.

In Reference Examples 4 and 5 in which the substrates B were heated to a temperature near the deformable temperature, the two substrates B, B could be bonded to each other, and the undulation of the bonding surfaces and warpage were deformed by the pressurizing force, and so the bonding surfaces were in much closer contact with each other, and the gap between the bonded surfaces was considerably improved, but not perfectly.

In Reference Examples 6 and 7 in which the substrates were heated to a temperature not lower than the deformable temperature of the substrate B, the two substrates B, B could be bonded to each other, and the undulation of the bonding surfaces and warpage of the substrates B and B were deformed by the pressurizing force, and so the bonding surfaces were in much closer contact with each other and no gap was formed in between the bonded surfaces; however, the surfaces in contact with a pressurizing member were deformed or the flow path was deformed.

Examples 1 and 2, and Comparative Examples 1 to 5

The substrate A and the substrate B were adopted as the first substrate and the second substrate, respectively, and these substrates were bonded to each other by performing an ultraviolet irradiation treatment step and a bonding step described below. In the substrate A adopted as the first substrate, a plurality of minute flow path forming portions were provided in advance. The flow path forming portion has a width of 150 μm, a depth of 150 μm, and a length of 20 mm.

Ultraviolet Irradiation Treatment Step:

Using a xenon excimer lamp, the bonding surface of each of the two substrates was irradiated with vacuum ultraviolet rays under the conditions that the irradiance was 40 mW/cm$^2$ and the irradiation time was 20 seconds (for the substrate A) or 30 seconds (for the substrate B).

Bonding Step:

The two substrates A, B were stacked so that their respective bonding surfaces were in contact with each other to obtain a stacked body (Stacking Step). Next, the two substrates A, B were bonded by pressurizing the stacked body under the conditions that the pressurizing force was 0.2 MPa, the pressurizing time was 300 seconds, and the heating temperature was set as described in Table 1.

The bonded body thus obtained was visually evaluated for bonded state. Further, the fractured cross section thereof was observed to confirm the presence or absence of the deformation of the flow path. The results are shown in Table 1.

In Comparative Examples 1 to 3, it was confirmed that although the two substrates A, B could be bonded to each other, the undulation of the bonding surfaces and warpage of the respective substrates could not be absorbed, and a gap was formed in a part of the bonded surfaces.

In Comparative Examples 4 and 5 in which the stacked body was heated to a temperature near the deformable temperature of the substrate (substrate B) having the lower deformable temperature, the two substrates A, B could be bonded to each other, and the undulation of the bonding surfaces and warpage were deformed by the pressurizing force, and so the bonding surfaces were in much closer contact with each other, and the gap between the bonded surfaces was considerably improved, but not perfectly.

In Examples 1 and 2 in which the stacked body was heated to a temperature not lower than the deformable temperature of the substrate (substrate B) having the lower deformable temperature, the two substrates A, B could be bonded to each other, and the undulation of the bonding surfaces and warpage of them were deformed by the pressurizing force, and so the bonding surfaces were in much closer contact with each other and no gap was formed in between the bonded surfaces. Furthermore, the surfaces in contact with the pressurizing member were not deformed and the flow path was not deformed.

Examples 3 and 4, and Comparative Examples 6 to 8

The substrate A and the substrate B were adopted as the first substrate and the second substrate, respectively, and these substrates were bonded to each other by performing a plasma gas treatment step and a bonding step described below. In the substrate A adopted as the first substrate, a plurality of minute flow path forming portions were provided in advance. The flow path forming portion has a width of 150 μm, a depth of 150 μm, and a length of 20 mm.

Plasma Gas Treatment Step:

Each of the substrates A and B was disposed at a position where the distance between the bonding surface thereof and a nozzle of a below-described atmospheric-pressure plasma apparatus shown in FIG. 4 was 3 mm, and the atmospheric pressure-plasma apparatus was operated under the following conditions, thereby performing a plasma gas treatment on each of the substrates A and B.

—Conditions—

Process gas (plasma gas): nitrogen gas (flow rate=150 L/min) and clean dry air (flow rate=1 L/min)

Input power: 1100 VA, voltage: 7.0 kV$_{p-p}$, frequency: 60 kHz

Irradiation time: 4 seconds (for the substrate A), or 5 seconds (for the substrate B)

Figure 4:
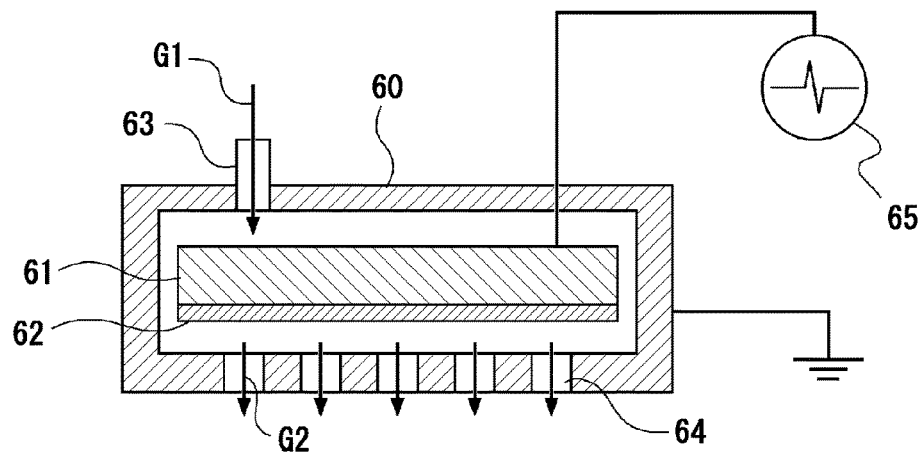
FIG. 4 is an explanatory cross-sectional view schematically illustrating a configuration in an example of an atmospheric-pressure plasma apparatus used in the present invention.

FIG. 4 is an explanatory cross-sectional view schematically illustrating a configuration in an example of the atmospheric-pressure plasma apparatus used in the present invention. The atmospheric-pressure plasma apparatus has a rectangular parallelepiped-shaped casing 60 formed of, for example, aluminum. A plate-shaped electrode 61 electrically connected to a high-frequency power source 65 is horizontally disposed within the casing 60. A dielectric layer 62 is formed on the lower surface of the electrode 61. In the atmospheric-pressure plasma apparatus of this example, the electrode 61 is a high-pressure side electrode, and the casing 60 is a ground side electrode.

A gas supply port 63 for supplying a process gas into the casing 60 is provided in the upper surface of the casing 60. A plurality of nozzles 64 are formed in the lower surface of the casing 60 for discharging the process gas, which has been converted into plasma by atmospheric pressure plasma in the casing 60, to the outside.

The material of the electrode 61 is Super Invar (a material in which a coating of alumina having a thickness of 500 μm is formed on the surface by thermal spraying), and the dimension of the surface thereof is 50 mm×300 mm. The distance between the casing 60 and the dielectric layer 61 is 0.5 mm.

In such an atmospheric-pressure plasma apparatus, the process gas G1 is supplied into the casing 60 from the gas supply port 63 under a pressure at or near atmospheric pressure. In this state, application of a high-frequency electric field between the electrode 61 and the casing 60 via the dielectric layer 62 by the high-frequency power source 65 generates a dielectric barrier discharge between the electrode 61 and the casing 60. As a result, the process gas G1 existing between the casing 60 and the dielectric layer 62 is ionized or excited into plasma. Then, the process gas G2 having been converted into plasma is discharged to the outside from the nozzle 64 of the casing 60, and comes into contact with the bonding surface of the substrate (not illustrated) disposed below the casing 60.

Bonding Step:

The two substrates A, B were stacked so that their respective bonding surfaces were in contact with each other to obtain a stacked body (Stacking Step). Next, the two substrates A, B were bonded by pressurizing the stacked body under the conditions that the pressurizing force was 0.2 MPa, the pressurizing time was 300 seconds, and the heating temperature was set as described in Table 1.

The bonded body thus obtained was visually evaluated for bonded state. Further, the fractured cross section thereof was observed to confirm the presence or absence of the deformation of the flow path. The results are shown in Table 1.

In Comparative Example 6, it was confirmed that although the two substrates A, B could be bonded to each other, the undulation of the bonding surfaces and warpage of the respective substrates could not be absorbed, and a gap was formed in a part of the bonded surfaces.

In Comparative Examples 7 and 8 in which the substrates were heated to a temperature near the deformable temperature of the substrate (substrate B) having the lower deformable temperature, the two substrates A, B could be bonded to each other, and the undulation of the bonding surfaces and warpage were deformed by the pressurizing force, and so the bonding surfaces were in much closer contact with each other, and the gap between the bonded surfaces was considerably improved, but not perfectly.

In Examples 3 and 4 in which the stacked body was heated to a temperature not lower than the deformable temperature of the substrate (substrate B) having the lower deformable temperature, the two substrates A, B could be bonded to each other, and the undulation of the bonding surfaces and warpage of them were deformed by the pressurizing force, and so the bonding surfaces were in much closer contact with each other and no gap was formed in between the bonded surfaces. Furthermore, the surfaces in contact with the pressurizing member were not deformed and the flow path was not deformed.

REFERENCE SIGNS LIST 10 stacked body
11 first substrate
11a bonding surface
15 second substrate
15a bonding surface
17 bonded body
17a bonded surface
19 ultraviolet light source
21 first microchip substrate
21a bonding surface
22 injection port
23 discharge port
24 flow path forming portion
25 second microchip substrate
25a bonding surface
27 microchip
27a bonded surface
50 stacked body
51 first microchip substrate
51a bonding surface
55 second microchip substrate
55a bonding surface
57 bonded body
59 ultraviolet light source
60 casing

TABLE 1

|  | First Substrate | | Second Substrate | | Heating Temperature | Evaluation Result | |
| --- | --- | --- | --- | --- | --- | --- | --- |
|  | Type | Deformable Temperature | Type | Deformable Temperature | During Pressurization | Bonding Defective Portion | Deformation of Flow Path |
| Reference Example 1 | Substrate B | 100° C. | Substrate B | 100° C. | 25° C. | Presence | Absence |
| Reference Example 2 | Substrate B | 100° C. | Substrate B | 100° C. | 50° C. | Presence | Absence |
| Reference Example 3 | Substrate B | 100° C. | Substrate B | 100° C. | 70° C. | Presence | Absence |
| Reference Example 4 | Substrate B | 100° C. | Substrate B | 100° C. | 80° C. | A Little | Absence |
| Reference Example 5 | Substrate B | 100° C. | Substrate B | 100° C. | 90° C. | A Little | Absence |
| Reference Example 6 | Substrate B | 100° C. | Substrate B | 100° C. | 100° C. | Absence | Slightly Deformed |
| Reference Example 7 | Substrate B | 100° C. | Substrate B | 100° C. | 110° C. | Absence | Presence |
| Comparative Example 1 | Substrate A | 120° C. | Substrate B | 100° C. | 25° C. | Presence | Absence |
| Comparative Example 2 | Substrate A | 120° C. | Substrate B | 100° C. | 50° C. | Presence | Absence |
| Comparative Example 3 | Substrate A | 120° C. | Substrate B | 100° C. | 70° C. | Presence | Absence |
| Comparative Example 4 | Substrate A | 120° C. | Substrate B | 100° C. | 80° C. | A Little | Absence |
| Comparative Example 5 | Substrate A | 120° C. | Substrate B | 100° C. | 90° C. | A Little | Absence |
| Example 1 | Substrate A | 120° C. | Substrate B | 100° C. | 100° C. | Absence | Absence |
| Example 2 | Substrate A | 120° C. | Substrate B | 100° C. | 110° C. | Absence | Absence |
| Comparative Example 6 | Substrate A | 120° C. | Substrate B | 100° C. | 25° C. | Presence | Absence |
| Comparative Example 7 | Substrate A | 120° C. | Substrate B | 100° C. | 80° C. | A Little | Absence |
| Comparative Example 8 | Substrate A | 120° C. | Substrate B | 100° C. | 90° C. | A Little | Absence |
| Example 3 | Substrate A | 120° C. | Substrate B | 100° C. | 100° C. | Absence | Absence |
| Example 4 | Substrate A | 120° C. | Substrate B | 100° C. | 110° C. | Absence | Absence |

As clear from the results described above, it was confirmed that, when the stacked body was heated at a temperature not lower than the deformable temperature of the substrate having a lower deformable temperature, the two substrates A, B could be bonded to each other in the state where the undulation of the bonding surfaces and warpage were deformed by the pressurizing force, and so the bonding surfaces were in much closer contact with each other and no gap was formed in between the bonded surfaces, and that the bonded body was obtained without deformation of the surfaces in contact with the pressurizing member and the flow path.

61 electrode
62 dielectric layer
63 gas supply port
64 nozzle
L vacuum ultraviolet rays
R flow path
S space

The invention claimed is:

1. A method of bonding substrates comprising bonding a first substrate and a second substrate, each formed of glass or a resin, to each other, wherein
the first substrate is formed of a material having a deformable temperature at which the substrate deforms and which is higher than a deformable temperature of the second substrate, the method comprises:
- a surface activation step of activating each of a bonding surface of the first substrate and a bonding surface of the second substrate;
- a stacking step of stacking the first substrate and the second substrate so that the respective bonding surfaces thereof are in contact with each other; and
- a deforming step of deforming the bonding surface of the second substrate to conform to a shape of the bonding surface of the first substrate, and the deforming step is performed by heating a stacked body of the first substrate and the second substrate obtained in the stacking step at a temperature not lower than the deformable temperature of the second substrate and lower than the deformable temperature of the first substrate.

2. The method of bonding substrates according to claim 1, wherein the two stacked substrates are pressurized in a direction in which they approach each other in the deforming step.

3. The method of bonding substrates according to claim 1, wherein the surface activation step is an ultraviolet irradiation treatment step of irradiating each of the bonding surface of the first substrate and the bonding surface of the second substrate with vacuum ultraviolet rays.

4. The method of bonding substrates according to claim 1, wherein the surface activation step is a plasma gas treatment step of bringing a process gas which has been converted into plasma by atmospheric pressure plasma into contact with each of the bonding surface of the first substrate and the bonding surface of the second substrate.

5. A method of producing a microchip, wherein a flow path forming portion is provided in at least one bonding surface of a first substrate and a second substrate in the first substrate and the second substrate, each formed of glass or a resin,
- the method comprising bonding the first substrate and the second substrate to each other by the method of bonding substrates according to claim 1 to obtain a microchip having a flow path through which a medium flows.

6. The method of producing a microchip according to claim 5, wherein the flow path forming portion is provided only in the bonding surface of the first substrate.

* * * * *